US00PP14920P2

(12) United States Plant Patent
Utecht

(10) Patent No.: US PP14,920 P2
(45) Date of Patent: Jun. 15, 2004

(54) GERANIUM PLANT NAMED 'FISDREAM'

(50) Latin Name: *Pelargonium peltatum*
Varietal Denomination: Fisdream

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,542

(22) Filed: Nov. 19, 2003

(30) Foreign Application Priority Data

Dec. 19, 2002 (CA) ..... PBR 02-3399

(51) Int. Cl.[7] ..... A01H 5/00

(52) U.S. Cl. ..... Plt./332

(58) Field of Search ..... Plt./332

*Primary Examiner*—Kent Bell
(74) *Attorney, Agent, or Firm*—Foley & Lardner LLP

(57) ABSTRACT

A new and distinct cultivar of geranium plant named 'Fisdream', particularly characterized by the combined features of large, red-purple, double flowers, large inflorescences, early and continuous flowering, medium green foliage with a narrow leaf zone, and bushy, trailing, fairly tall plant habit.

1 Drawing Sheet

Genus and Species of the Plant Claimed: Hybrid of the species *Pelargonium peltatum* L'Héritier
Variety Denomination: 'Fisdream'

BACKGROUND OF THE INVENTION

The present invention comprises a new and distinct cultivar of geranium, botanically known as *Pelargonium peltatum,* and hereinafter referred to by the cultivar name 'Fisdream'.

'Fisdream' is a product of a planned breeding program which had the objective of creating new ivy geranium cultivars with purple, double-type flowers, zoned foliage, and relatively vigorous, but well-branched growth habit.

'Fisdream' originated from a hybridization made by the inventor, Angelika Utecht, in a controlled breeding program in Hillscheid, Germany, in 1998. The female parent was an unpatented hybrid seedling, No. 96/1734/2, having violet, double flowers; foliage with distinct zonation, and vigorous growth. The male parent of 'Fisdream' was the unpatented hybrid seedling No. 96/1631/7, characterized by red, single-type flowers, zoned foliage, and relatively strong growth.

'Fisdream' was selected as one flowering plant within the progeny of the stated cross by Angelika Utecht in 1999 in a controlled environment in Moncarapacho, Portugal.

The first act of asexual reproduction of 'Fisdream' was accomplished when vegetative cuttings were taken from the initial selection in the fall of 1999, in a controlled environment in Moncarapacho, Portugal, by, or under the supervision of, Angelika Utecht.

Horticultural examination of plants grown from cuttings of the plant initiated in May 2000, in Hillscheid, Federal Republic of Germany, and continuing thereafter, has demonstrated that the combination of characteristics as herein disclosed for 'Fisdream' are firmly fixed and are retained through successive generations of asexual reproduction.

'Fisdream' has not been observed under all possible environmental conditions. The pheno-type may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisdream' in combination distinguish this geranium as a new and distinct cultivar:

1. Bright red-purple colored, double flowers;
2. Large flowers and large, almost semi-spherically shaped inflorescences;
3. Medium-green foliage, large leaves with distinct lobes and narrow zonation;
4. Fairly vigorous growth, trailing, moderately tight, bushy plant habit; and
5. Early spring flowering response.

Of the many commercial cultivars known to the present inventor, the most similar in comparison to 'Fisdream' is the patented variety 'Fislulu' (U.S. Plant Pat. No. 12,228). In comparison to 'Fislulu', 'Fisdream' has a brighter and more reddish hue of flower color and distinctly taller plant habit.

BRIEF DESCRIPTION OF THE DRAWINGS

The accompanying photographic drawing shows typical flower and foliage characteristics of 'Fisdream' with colors being as true as possible with an illustration of this type.

The photographic drawing on the top of the sheet shows a 'Fisdream' plant in a hanging basket and the photographic drawing on the bottom of the sheet shows a branch end of 'Fisdream' with leaves, buds, and inflorescences.

DETAILED BOTANICAL DESCRIPTION

The measurements were taken in Hillscheid, Germany, in mid May, 15 weeks after planting of rooted cuttings. The plants were growing in 14-cm pots, they had been pinched once.

In the following description color references are made to The Royal Horticultural Society Colour Chart. The color values were determined indoors from plants growing in a green-house in May 2003 in Hillscheid, Germany.

INFLORESCENCE

Umbel:

*Shape.*—Nearly semi-spherical.
*Average diameter.*—119 mm.
*Average depth.*—About 65 mm.
*Peduncle length.*—167 mm.
*Peduncle color.*—Light green, RHS 143 B.
*Pedicel.*—39 mm in length, with a spur near the lower end.
*Pedicel color.*—Mainly green, RHS 143 A to RHS 143 B, partly brownish, RHS 184 A.
*Number of flowers per umbel.*—8–13.

Corolla:

*Average diameter.*—57 mm.
*Form.*—Double-type.
*Shape.*—Outline oval to round, with the inner petals somewhat smaller in size.
*Number of petals.*—20–23.
*Shape of petals.*—Obovate, base attenuate, upper end is truncate or rounded, margin is entire.
*Size of petals.*—Upper petals: 33–34 mm long, 22–24 mm wide, lower petals: 27–28 mm long, 21–22 mm wide.
*Color (general tonality from a distance of three meters)* .—Bright red-purple.
*Color of upper petals.*—Main part RHS N66A.
*Markings of upper petals.*—Two dark purple veins, RHS 187 B.
*Color of lower petals.*—Between RHS N66A and N66B.
*Markings of lower petals.*—None.
*Color of lower surface of petals.*—RHS 61 C to N 66 C.
*Color of sepals.*—Outer surface: light green, RHS 144 B, upper sepal brownish infused, RHS 184 B; inner surface: light green, RHS 144 B.
*Number of sepals.*—5.
*Shape of sepals.*—Linear to lanceolate, acute to acuminate tip, base sessile, surface with very little pubescence, margin entire.
*Size of sepals.*—15–16 mm long, 5 mm wide for the largest upper sepal, 3–4 mm in width for the other sepals.

Bud: (just prior to petals unfolding):

*Shape.*—Elliptical.
*Color of sepals.*—Light green, RHS 144 B.
*Color of petals.*—RHS 61 C to 61 B.
*Length.*—24 mm.
*Width.*—10 mm.

REPRODUCTIVE ORGANS

*Androecium.*—4–5 fertile anthers, moderate pollen, yellow-orange, RHS 25 A, lower side of anthers blackish, RHS 187 A, filaments white, RHS 155 D, to light-pink, RHS 52 D.
*Gynoecium.*—One pistil, whitish style, RHS 155 D to 65 D, stigma 5–6-lobed stigma, dark-red, RHS 53 A.
*Fertility/seed set.*—No seed set observed.

Spring flowering response period: In Hillscheid, Germany, in 2001 plants had on average 1.1 flowers opened 12 weeks after planting of rooted cuttings (pinched plants)

Outdoor flower production: Continuously and moderately rich flowering, the flower count in 2003 in Hillscheid, Germany, indicated about 3 inflorescence per plant in mid May Durability: Relatively good stability of flower color, little fading fair rain resistance, good heat tolerance Lastingness of the individual flower: About 8 days at 18° C.

Fragrance: None

PLANT

Foliage:

*Shape.*—Ivy-shaped, almost star-shaped, with cordate base, with the gap between the lowest lobes mostly closed, relatively strong lobes.
*Margin.*—Mostly entire, occasionally single notches near the tips of lobes.
*Texture.*—Upper surface smooth, glossy.
*Size of leaf.*—95 mm wide, 52 mm long.
*Color of upper surface.*—Medium green, approximately RHS 137 D.
*Zonation.*—A narrow ring, brown, closest to RHS 166 A.
*Color of lower surface.*—RHS 137 D.
*Petioles.*—40–50 mm long, 2–2.5 mm diameter, light green in color, closest to RHS 143 C.

General appearance and form:

*Stem color.*—Light green, RHS 143 B.
*Internode length.*—45–64 mm.
*Branching pattern.*—10–13 branches.
*Size of plants.*—24 cm (15-week-old plants, as described); 90 cm (30-week-old plants, around September 1), measured from the top of the soil (base of the main stem) to the tips of the branches, without inflorescences.

I claim:

1. A new and distinct cultivar of geranium plant named 'Fisdream', as described and illustrated herein.

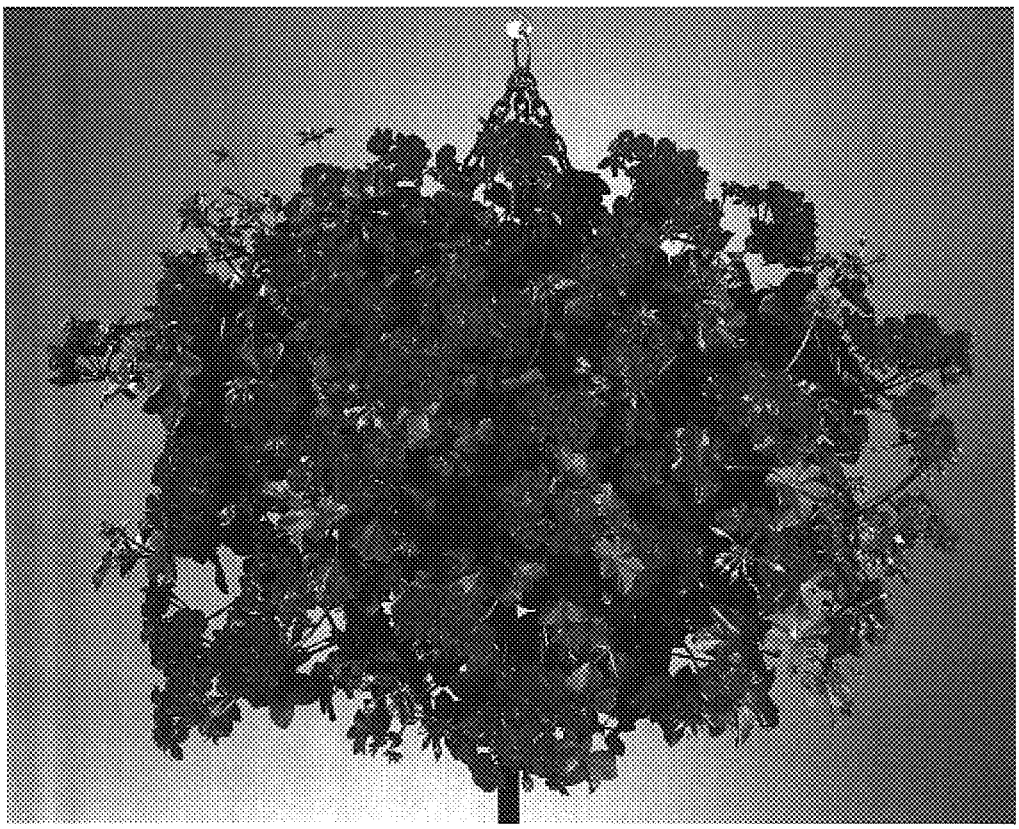
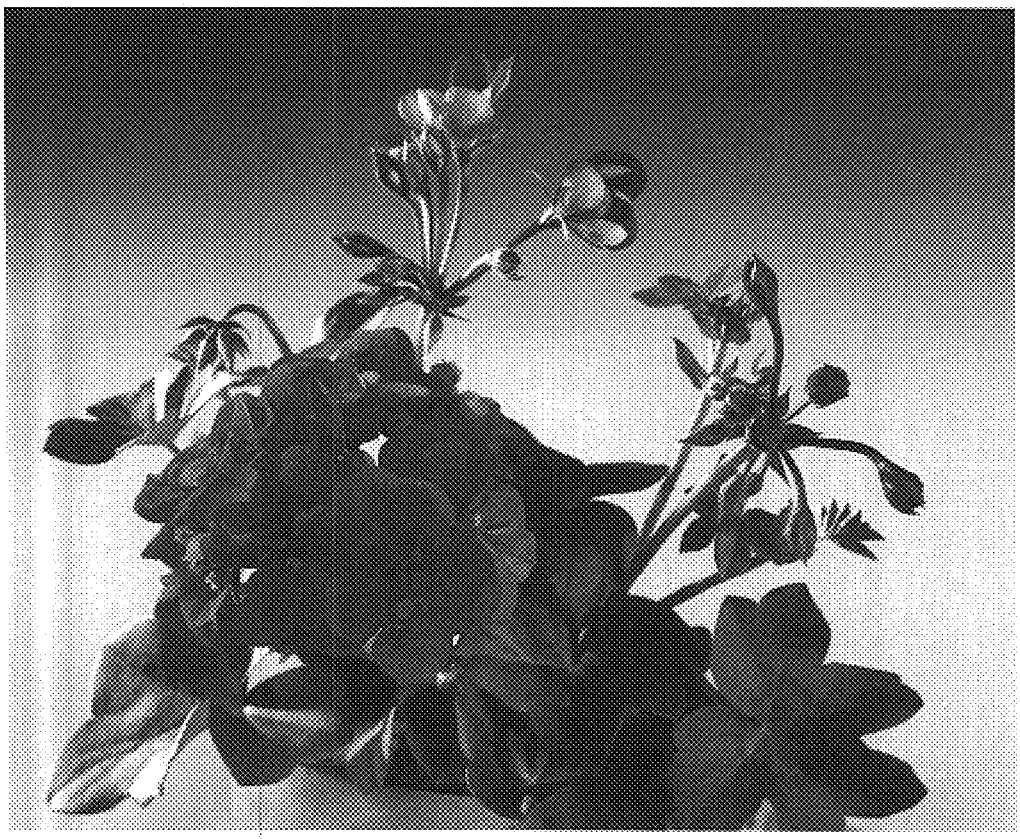

* * * * *